United States Patent [19]

Ives et al.

[11] Patent Number: 5,222,503
[45] Date of Patent: Jun. 29, 1993

[54] AMBULATORY ELECTROENCEPHALOGRAPHY SYSTEM

[75] Inventors: John R. Ives, Lexington; Norman R. Mainwaring, Boston, both of Mass.

[73] Assignee: Beth Israel Hospital Association, Boston, Mass.

[21] Appl. No.: 690,733

[22] Filed: Apr. 24, 1991

[51] Int. Cl.⁵ .......................................... A61B 5/0476
[52] U.S. Cl. .................................................... 128/731
[58] Field of Search ............................... 128/731-732

[56] References Cited

U.S. PATENT DOCUMENTS

| | | | |
|---|---|---|---|
| 4,519,398 | 5/1985 | Lisiecki et al. | 128/710 |
| 4,603,703 | 8/1986 | McGill et al. | 128/731 |
| 4,610,259 | 9/1986 | Cohen et al. | 128/731 |
| 4,850,367 | 7/1989 | Rantala | 128/670 |
| 4,878,498 | 11/1989 | Abrams et al. | 128/419.5 |
| 4,920,489 | 4/1990 | Hubelbank et al. | 364/413.06 |
| 5,012,411 | 4/1991 | Policastro et al. | 364/413.06 |
| 5,029,590 | 7/1991 | Allain et al. | 128/710 |
| 5,038,782 | 7/1991 | Gevins et al. | 128/644 |

OTHER PUBLICATIONS

Lettich et al., "A simplified circuit for stimulus artifact suppression", Electroencephalography and Clinical Neurophysiology, vol. 39, No. 1, pp. 85-87, Jul. 1975.

"Ambulatory EEG Monitoring", John Ebersole, Raven Press, 1989, Chapters 1 and 2.

"Clinical Usefulness of Ambulatory EEG", John S. Ebersole, Samuel L. Bridgers, Marshall J. Keilson, American Academy of Neurology 1990 Annual Meeting Seminar 267.

"Ambulatory Outpatient EEG Monitoring" (A1-A2), John R. Ives, Donald L. Schomer, American Academy of Neurology Annual Course #450 (Apr.-May 1990).

Primary Examiner—Lee S. Cohen
Assistant Examiner—Jeffrey R. Jastrzab
Attorney, Agent, or Firm—Reed Smith Shaw & McClay

[57] ABSTRACT

An ambulatory electroencephalography (EEG) system includes a self-powered recording apparatus adapted to be worn by a patient. The recording apparatus includes an A/D converter and a digital memory capable of storing digital data representing analog waveform signals derived from a large number of electrodes secured to the patient. Recording of digital waveform data is governed by a controller, which upon the occurrence of a neurologically significant event (such as actuation of a switch by the patient or detection of EEG waveforms indicating a seizure state) causes the storage of waveform data over an interval immediately preceding the event and immediately following the event.

53 Claims, 12 Drawing Sheets

FIG. 4a
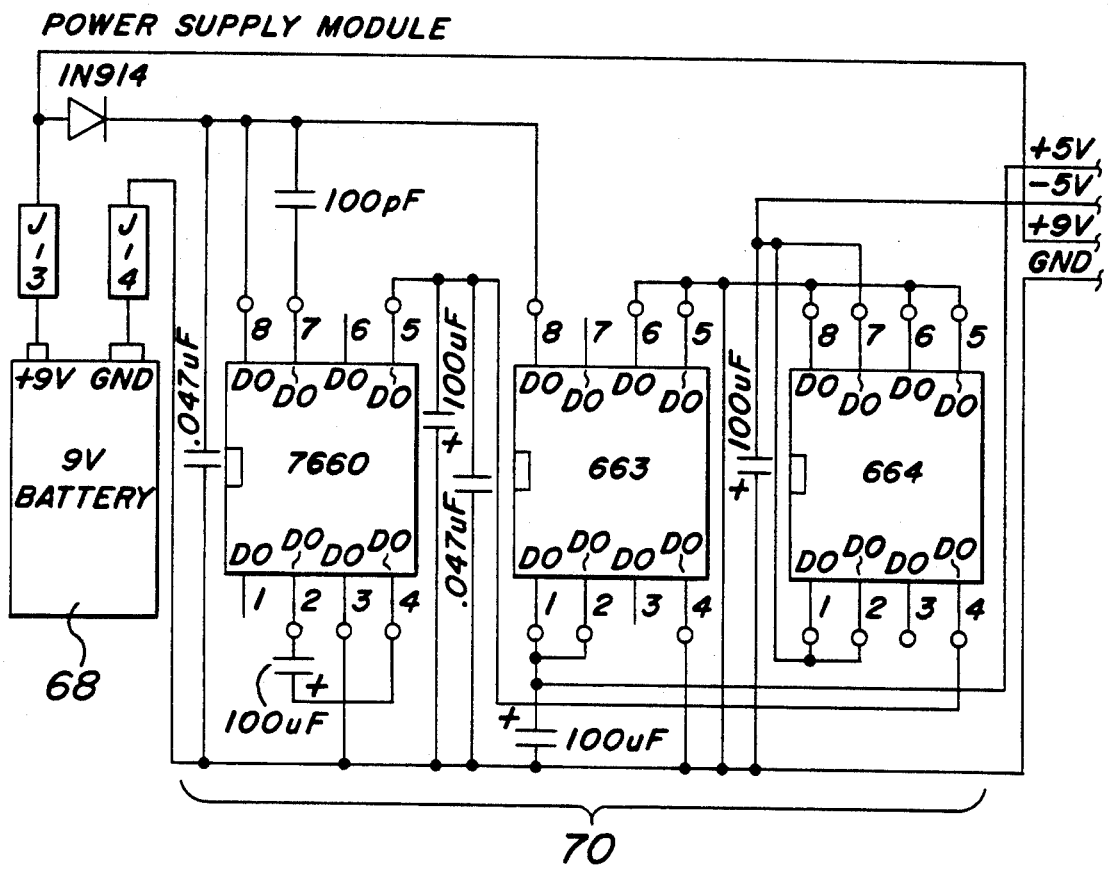
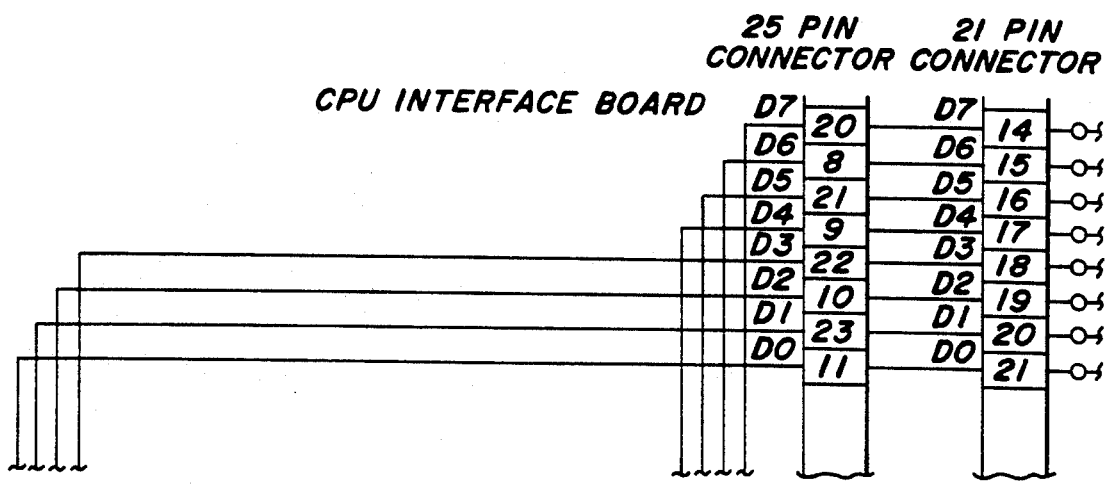

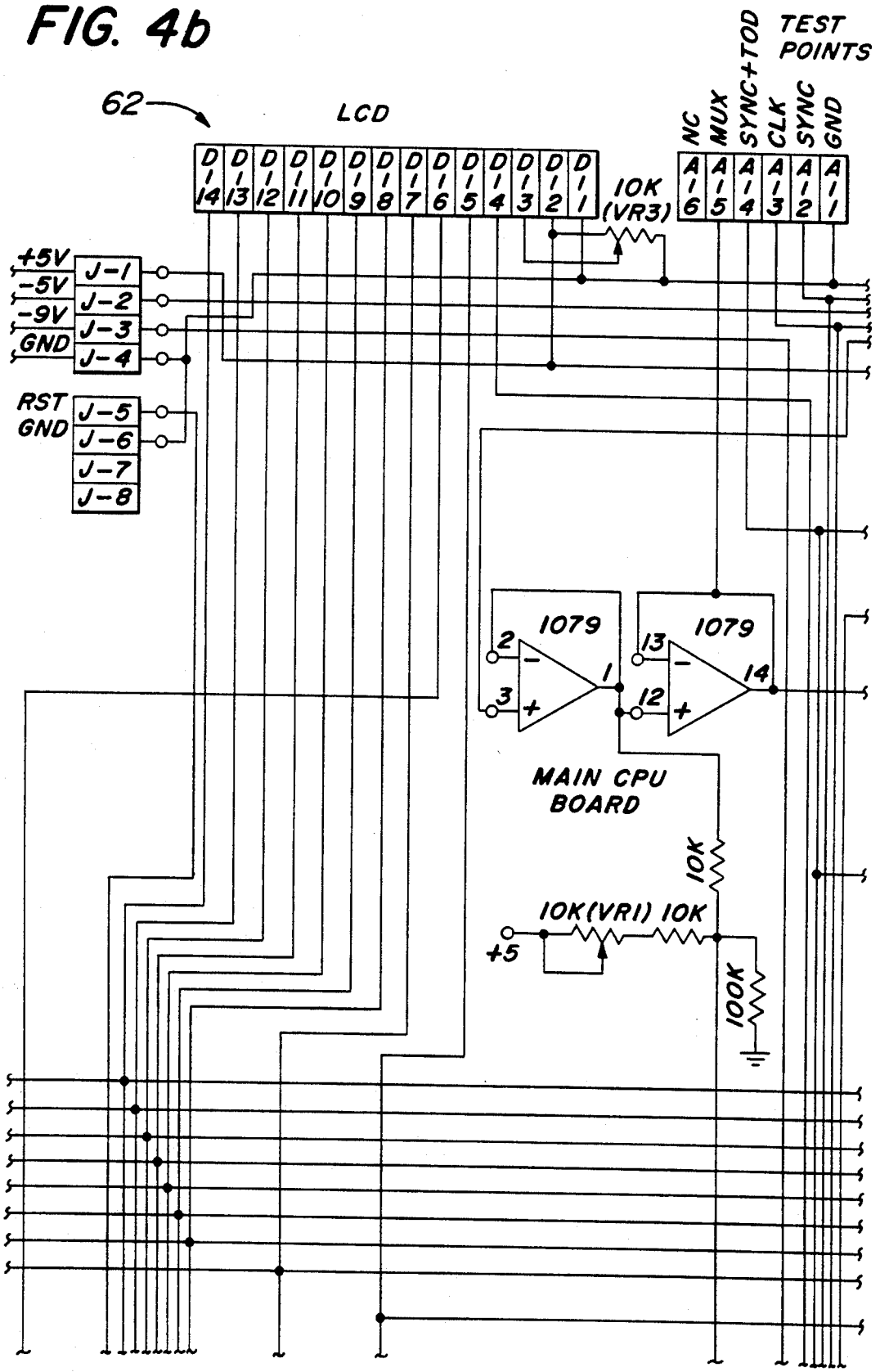

FIG. 4c
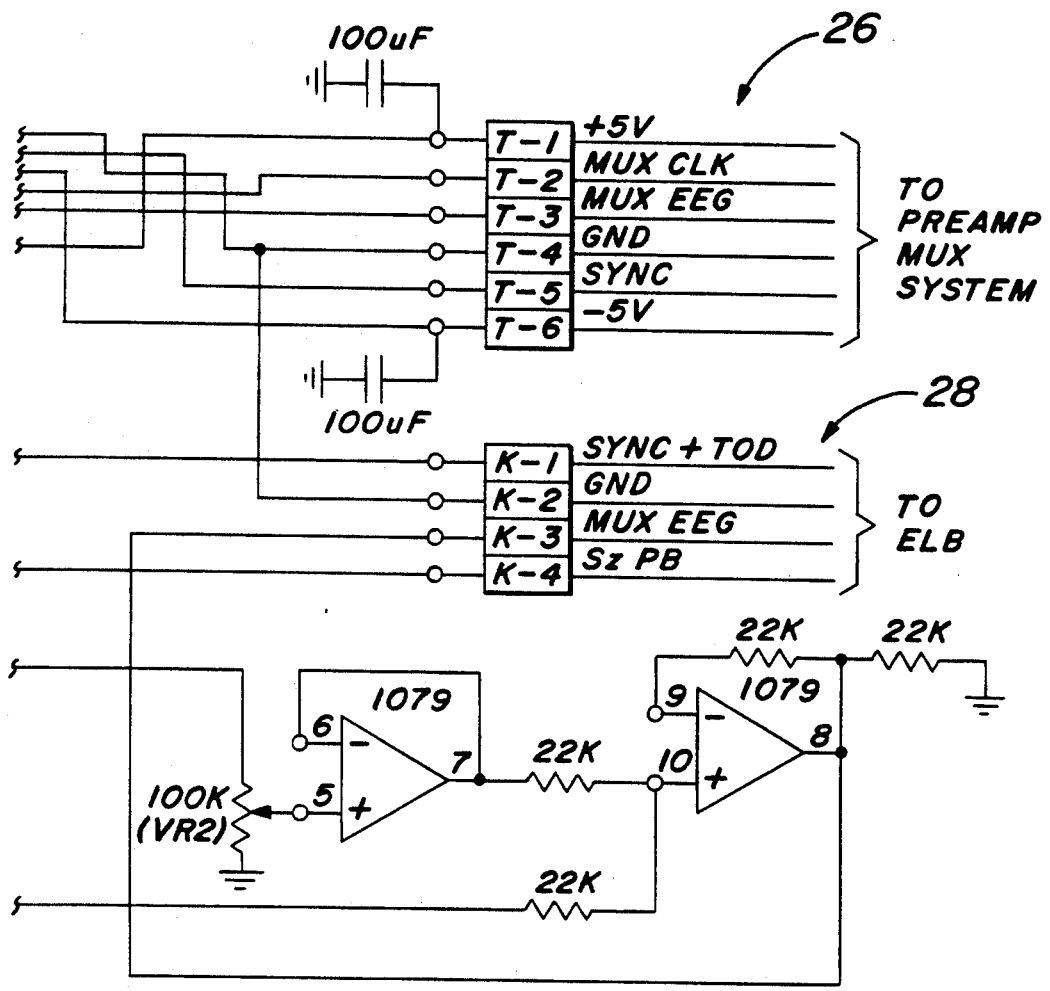
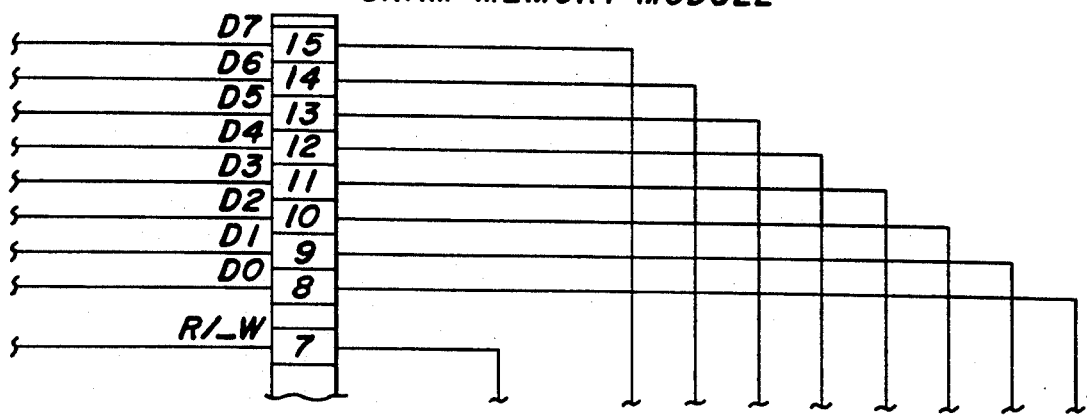
SRAM MEMORY MODULE

FIG. 6

MICROPROCESSOR

| EEPROM (512 BYTES) FIRMWARE | RAM (1K BYTES) DOWN LOADABLE MODULE (DLM) | |
|---|---|---|
| ESTABLISH HOST COMMUNICATION<br>TIMING OF MULTIPLEXER<br>INTERRUPT VECTORS<br>CONFIGURES I/O PINS<br>LOADS DLM<br>RUNS DLM | FUNCTIONS<br>MAINTAINS REAL TIME CLOCK<br>MAINTAINS DELAY BUFFER<br>PUTS T.O.D. ON SYNC<br>MONITORS BATTERY VOLTAGE<br>WATCH DOG TIMER<br>ERROR RECOVERY | PATIENT PARAMETER BLOCK<br>PATIENT NAME<br>TIME OF DAY<br>TECHNICIAN<br>EVENT COUNTER<br>MONTAGE<br>BATTERY VOLTAGE STATUS<br>NUMBER OF EVENTS SAVED<br>PRE & POST EVENT TIME |

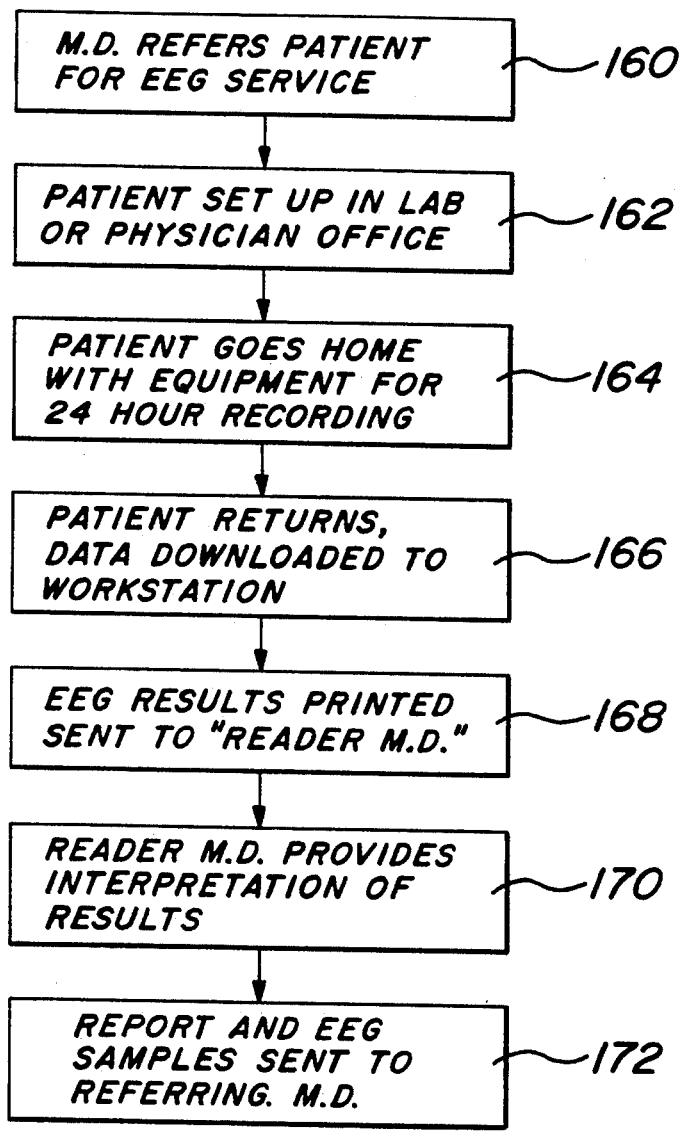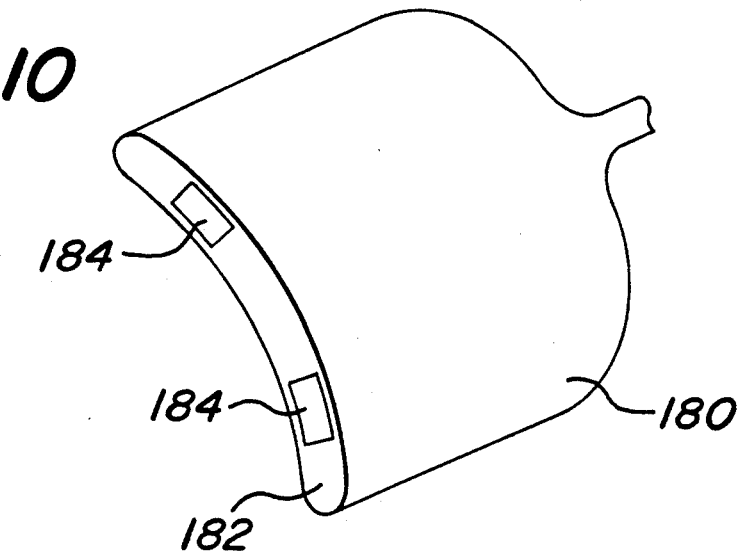

AMBULATORY ELECTROENCEPHALOGRAPHY SYSTEM

FIELD OF THE INVENTION

This invention relates to ambulatory patient neurological monitoring. More particularly, this invention relates to ambulatory electroencephalographic (EEG) monitoring. Still more particularly, this invention relates to a method and apparatus ("system") for reliably producing high quality, multiple channel brain wave records for a patient who is not confined to a hospital or other inpatient facility during the monitoring procedure.

BACKGROUND OF THE INVENTION

EEG or brain wave monitoring is a well established technique for evaluating brain function to assist in diagnosis of neurological disorders. Such monitoring has been most reliably performed on an inpatient basis such as in a hospital or similar facility. Monitoring in such a setting has many advantages. Hospitals and similar facilities have access to the large and expensive EEG machines typically needed for such monitoring. They also have facilities for caring for the patient on a long term basis, such monitoring typically being performed for a period on the order of ten days. Trained electrophysiologists are available in such facilities to secure electrodes to the patient, attach the electrodes to an EEG machine, and periodically observe the monitoring apparatus during the procedure to ensure that useful results are obtained. The ability in such a setting to shield the apparatus from stray signals which might interfere with the very small signals to be detected, and the restriction of patient movement to reduce movement-generated artifacts, contribute to the likelihood of obtaining useful results. Such inpatient monitoring is often the most desirable method for obtaining EEG data for diagnosis. However, it is a time consuming and expensive procedure, and the availability of inpatient facilities for such monitoring is often limited.

EEG monitoring is also performed on an outpatient basis, such as in a neurologist's office, hospital outpatient facilities, or the like. Outpatient EEG monitoring is typically performed for a short time, e.g. less than an hour, as a routine EEG study. Such routine studies may yield equivocal results or fail to detect brainwaves due to episodic events, but are useful to provide baseline data and as a relatively low cost screening procedure to determine whether a patient should undergo long term inpatient monitoring.

In order to provide some of the benefits of long-term monitoring without the inconvenience and expense of inpatient monitoring, various attempts have been made to develop systems for ambulatory EEG monitoring, i.e. monitoring using portable apparatus coupled to the patient, while the patient is not confined to a hospital or other medical facility. Such monitoring is highly desirable from a cost and convenience standpoint, in those situations where patient confinement during the monitoring procedure is not otherwise required. For instance, a patient may complain of episodic events such as "funny spells". A routine EEG study may provide normal results, and it will then be unclear whether this result is due to the fact that the patient has routine brain function or that no episodic events occurred during the routine EEG procedure. It would be highly desirable to obtain further EEG information without the expense, delay, and inconvenience of inpatient monitoring.

Existing ambulatory EEG systems to address these needs have been subject to a number of drawbacks limiting their use and usefulness. These drawbacks stem generally from the extremely large amounts of data which must be obtained for useful EEG monitoring and the difficulty in obtaining high quality data. The patient being monitored is not subject to the restrictions of an inpatient setting. To be useful, an ambulatory EEG system should have the capability of storing data occurring over a period on the order of day or more. During the monitoring period, it should have the capability of storing waveform data regarding at least several events, each of which may be several minutes in duration. It should further have the ability to store waveform data occurring immediately prior to an event. Such a monitoring system should also have the capability of simultaneously storing waveform data from a large number of channels during each event. One professional association in the field has issued guidelines specifying that at least 16 channels of waveform data should be obtained in inpatient EEG monitoring. However, because of the lack of adequate available ambulatory systems meeting these guidelines, no such guidelines have been issued for ambulatory EEG monitoring.

In order to accommodate the large amount of EEG data to be stored, prior art systems have generally relied upon magnetic tape recorders as the storage medium. One of the inventors of the present invention has developed such a system, which has been sold by Telefactor Corporation under the designation "A1-A2". The shortcomings of tape recorders for storing data generated in ambulatory patient monitoring is known, and is described for instance in U.S. Pat. No. 4,519,398 issued May 20, 1985 to Lisiecki et al. Generally, these shortcomings include size, weight, power consumption reliability, and quality of stored signals, which are typically stored as analog signals.

Various attempts have been made to limit the use of tape recorders in ambulatory physiological monitoring. For instance, one prior art ambulatory EEG system uses a combination of solid state memory and magnetic tape storage. This system responds to switch actuation, typically by the patient when an event begins, and records on magnetic tape the brain wave signals received for a predetermined time after switch actuation. Solid state memory is employed as a buffer for temporarily holding data. Incoming signals are stored in the memory configured as a first-in first-out device; when the event switch is actuated, the contents of the memory are latched to reflect the pre-actuation brain wave signals which may be relevant to the onset of the event. The latched data is then transferred to magnetic tape, so that the solid state memory is available to store pre-actuation data for the next event. All permanently stored data is stored on magnetic tape, and the solid state memory serves merely as a convenient means for temporarily capturing data occurring prior to switch actuation.

Lisiecki et al. U.S. Pat. No. 4,519,398 discloses a system for ambulatory monitoring of cardiac information, particularly heart rate and blood pressure information. The amount of data required to be stored in such monitoring is extremely limited. In order to store even this limited amount of data in a solid state memory, Lisiecki et al. require that the signals from the patient physiological sensors be highly processed prior to storage. Lisiecki et al do not store waveform data for the parameters being monitored; rather, numerical data representing heart rate and blood pressure computed from the waveform data relating to multiple channel EEG monitoring. Moreover, although Lisiecki et al. state that the disclosed system eliminates the use of a tape recorder, they contradictorily state that the equipment required to be used with the system of their invention includes a magnetic tape recorder, in column 2 line 23 through column 3 line 25.

Existing ambulatory EEG monitoring systems also have shortcomings in their mode of acquisition, analysis, and distribution of monitoring results. After a physician prescribes ambulatory EEG monitoring, the patient may be outfitted with monitoring equipment by a nurse or other office staff member who is not well trained in EEG. The patient goes home wearing the monitoring equipment, and data is recorded on magnetic tape over a period of a day or so. The equipment is then removed from the patient, and the tape is sent to an electroencephalographer for analysis of the captured data. This may include an initial high speed audio or video review of the tape by an EEG technician to attempt to locate portions of potential neurological significance. This initial review is performed to reduce the amount of data to be printed and reviewed by an electroencephalographer, but may result in significant events being overlooked. The waveform data on the identified portions of the tape is then printed, typically by a moving-pen type charter or plotter. The quality of waveforms produced by such devices is generally poor. The printed waveforms corresponding to identified potential events are then reviewed by an electroencephalographer, who prepares narrative report which is sent to the referring physician. The referring physician receives only the narrative report; waveform printouts on chart paper are difficult to store in patient files and are stored, if at all, only by the electroencephalographer. If the referring physician has any questions or requires additional information, he generally must call the electroencephalographer and attempt to satisfy his concerns by a telephone discussion without the benefit of waveform printouts.

Extensive information has been published regarding EEG monitoring in general and ambulatory EEG monitoring in particular. For further information regarding existing ambulatory EEG monitoring, including monitoring systems, procedures, clinical tests, indications, and limitations, reference may be made to "Ambulatory EED Monitoring", John S. Ebersole, Raven Press, 1989; "Clinical Usefullness of Ambulatory EEG", John S. Ebersole, Samuel L. Bridgers, Marshall J. Keilson, American Academy of Neurology 1990 Annual Meeting Seminar 267; and "Ambulatory Outpatient EEG Monitoring (A1-A2)", John R. Ives and Donald L. Schoner, American Academy of Neurology Annual Course #450 (April-May, 1990). These publications provide further background to the present invention; since much of their disclosures is pertinent to the present invention, they are incorporated herein by reference to the extent necessary to render this specification complete.

SUMMARY OF THE INVENTION

It is therefore a general object of the invention to provide an ambulatory EEG monitoring system which avoids the above-described problems of the prior art systems.

It is another object of the invention to provide such a system having improved quality of stored data.

It is another object of the invention to provide such a system in which storage of data corresponding to patient movement artifacts and other non-neurological events is reduced.

It is another object of the invention to provide such a system in which waveform data is stored, analyzed, and output in digital form.

It is another object of the invention to provide such a system in which waveform data is output in a form suitable for inclusion in the patient files of the referring physician.

It is another object of the invention to provide such a system in which data is stored for a large number of channels.

It is another object of the invention to provide such a system which is simple, rugged, reliable, and inexpensive.

In accordance with the foregoing objects, the system of the invention includes ambulatory EEG apparatus having solid state memory capable of storing EEG waveform data for a large number of channels for a number of events occurring over a period which may be a day or more. The apparatus stores waveform data in response to actuation of switch by a person when it is believed that a neurologically significant event is occurring, and stores data for a period both prior to and after switch actuation. In a preferred embodiment, the system also stores waveform data periodically and in response to data analysis under a software algorithm indicating of the occurrence of a neurologically significant event. Digitally stored waveform data permits convenient review of all data by an electroencephalographer to ensure that all significant events are identified. Waveform data is digitally printed by a laser printer, which provides high quality traces in a form which can be easily transmitted to the referring physician for reference in reviewing the electroencephalographer's narrative report and for inclusion in the referring physician's patient file.

Other objects and features of the invention will become apparent upon review of the following specification and claims and the drawings.

BRIEF DESCRIPTION OF THE DRAWINGS

FIG. 6 is a software block diagram for the preferred recording apparatus;

FIG. 8 is a flow diagram of a method according to the invention;

FIG. 10 is a perspective illustration of a portion of a transducer assembly.

DETAILED DESCRIPTION OF THE PREFERRED EMBODIMENT

Figure 1:
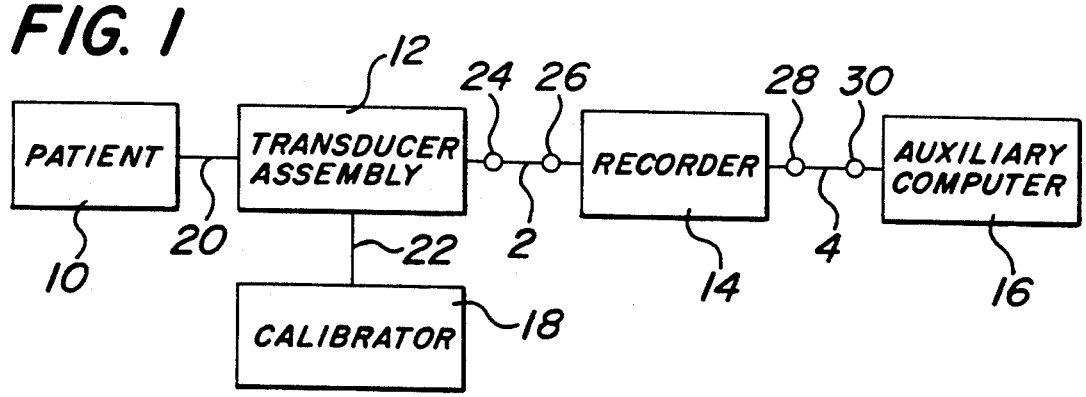
FIG. 1 is a general block diagram of the apparatus of the invention.

FIG. 1 is a general block diagram illustrating the system of the present invention. A patient 10 to be monitored is coupled to an ambulatory EEG monitoring system comprising a transducer assembly 12 and a solid state recording and control apparatus 14, hereinafter referred to as recorder 14. Although it may become possible to provide a single piece of equipment providing the transducer and recorder functions, due to present limitations of technology transducer assembly 12 and recorder 14 are desirably provided as separate pieces of equipment interconnected by a communication channel 2. Electrical signals relating to brainwave and other physiological data are stored in recorder 14.

Transducer assembly 12 includes patient monitoring electrodes for producing electrical signals representing physiological conditions of the patient, including EEG signals or brainwaves. Such electrodes are coupled to the patient to be monitored at predetermined locations, or in a "montage", in accordance with the monitoring procedure desired to be performed. Desirably, electrodes are provided to perform monitoring of at least about 16 channels of EEG data; other physiological parameters may also desirably be simultaneously monitored, such as EKG parameters. An input 22 to transducer assembly 12 may be provided, to enable signals generated by a calibrator 18 to be applied to the system for calibration and checking purposes.

Desirably, the electrodes are cup-shaped silver-silver chloride electrodes, which are glued at appropriate locations to the scalp of the patient 10 being monitored to provide the input 20 to the transducer assembly. To minimize stray signals and movement artifacts in the measurement of the very small EEG signals, transducer assembly 12 is desirably located immediately adjacent to the patient's head. However, with presently available technology it is impossible to include the recorder function in a structure which is mountable on a patient's head. Therefore a separate recorder 14 is provided, having an input 26 coupled to the output 24 of the transducer assembly by communication channel 2. Thus, transducer 12 produces signals at its output 24 which are suitable for transmission from the head-mounted transducer assembly 12 to a recorder 14 which may be carried elsewhere on the body of the patient while ambulatory. Applicants prefer a recorder 14 which is adapted to be worn at the waist.

Recorder 14 includes a solid state memory sufficient to hold waveform data for desirably about 16 channels of EEG data for intermittent recording over a period of several hours to several days. Such a memory is unaffected by patient movement, unlike tape recorders. Recorder 14 includes an input/output port (I/O port) 28, to enable communication with an auxiliary computer 16 via a communication channel 4 and an I/O port 30 associated with the auxiliary computer. As will be described more fully below, auxiliary computer 16 may be portable but is generally not adapted to be worn by the patient during ambulatory monitoring. Several different functions may be performed by auxiliary computer 16, and these functions may be implemented by different computers. The recorder 14 may be coupled to a first auxiliary computer during set up of the apparatus to download patient data and operating instructions; a second auxiliary computer in the home environment to augment data storage capabilities and to provide for automatic event detection; and a third auxiliary computer after monitoring is complete, to transfer the recorded information for processing, analysis, permanent storage, and generation of printed outputs.

Figure 2:
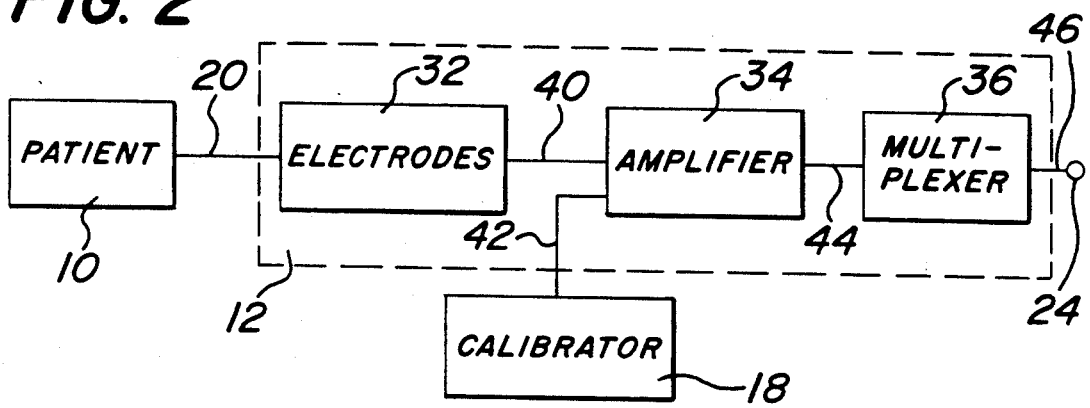
FIG. 2 is a block diagram including the transducer assembly of FIG. 1.

FIG. 2 shows a more detailed block diagram including the transducer assembly 12. Transducer 12 includes amplifier 34; desirably, one amplifier is provided for each channel of physiological data to be obtained. Amplifier inputs 40 are coupled to appropriate sensing or reference electrodes 32 coupled to the patient. In order to facilitate the transmission of amplifier output signals to the recorder, the amplifier outputs 44 are coupled to the input of multiplexer 36, whereby the output signals at multiplexer output 46 may be transmitted over a common communication channel.

Figure 3:
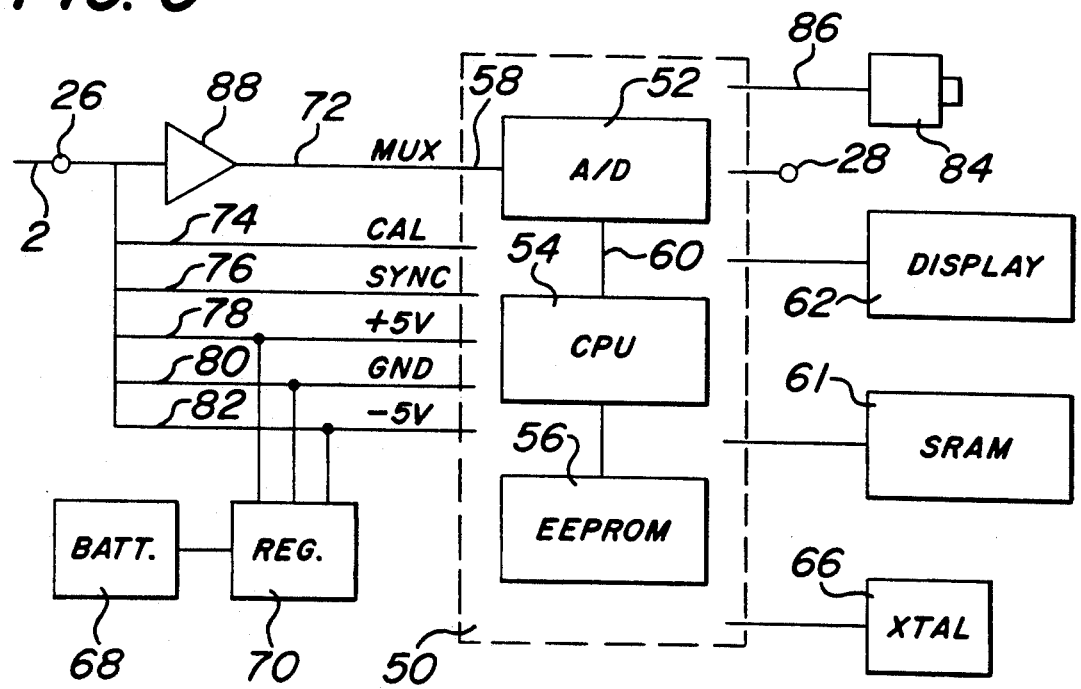
FIG. 3 is a block diagram of the preferred recording apparatus of the invention.

FIG. 3 is a block diagram of the preferred recording apparatus of the present invention. Recorder 14 operates under control of microprocessor 50, which includes a central processing unit 54, program memory 56 such as EEPROM, and analog-to-digital ("A/D") converter 52. Multiplexed EEG signals from transducer 12 are received at I/O port 26. Such signals are buffered by amplifier 88 and coupled by MUX line 72 to the input 58 of A/D converter 52. Such analog input signals are digitized by A/D converter 52 and stored in static RAM 61 under control of CPU 54. RAM 61 desirably has at least about 1 megabyte of memory capacity, and preferably at least 4 megabytes of memory capacity. A push-button 84 is coupled to microprocessor 50 by lines 86, and actuation of the push-button 84 causes storage of data in static RAM 61. Such stored data includes data occurring both prior to and after actuation of the push-button. Accordingly, the patient or another person can initiate data storage when the patient is experiencing a "funny spell" or other symptom.

Operating power for recorder 14 is provided by battery 68, which is coupled to a regulator circuit 70 to generate +5 V, GND, and −5 V supply potentials 78, 80, and 82, respectively. In addition to powering the recorder 14, these potentials are also coupled via port 26 to the transducer assembly 12. Communication channel 2 also couples CLK line 74 and SYNC line 76 to the microprocessor 50 and the transducer assembly 12, to control transfer of information.

Microprocessor 50 drives an alphanumeric display 62, such as an LCD display, which may be used to indicate the number of events which have been recorded, battery condition, patient information, set up parameters, and the like. A crystal 66 is incorporated into a clock circuit to provide a time base for microprocessor 50. Microprocessor 50 also provides an output port 28 for interchanging information with auxiliary computers.

FIG. 4 shows a schematic diagram of the preferred recorder 14. A microprocessor 50, type MC68HC11F1, provide a CPU 54, and A/D converter 52, and EEPROM 56. Static RAM 61 comprises 32 IC's, each of which is a type HM628128 128 k×8 static RAM. As space is a substantial concern in portable, patient-worn equipment, applicant's have developed a novel means for interconnecting these IC's. Rather than mounting them in a planar fashion to a circuit board, applicants have instead stacked the IC's vertically. Almost all corresponding pins of the IC's are to be connected together in the memory circuit; the pins overlap one another when stacked vertically, and can be soldered together. Corresponding pins which are not to be connected together on all IC's, such as chip select pins, may be bent outwardly and appropriately connected by wires soldered to the pins. Applicants have found it desirably to configure the memory in two such stacks of 16 IC's each.

Other aspects of the operation of the operation of the circuit of FIG. 4 will no doubt be apparent to a person of ordinary skill in the art upon inspection of this detailed schematic, and will not be further discussed here.

Figure 5:
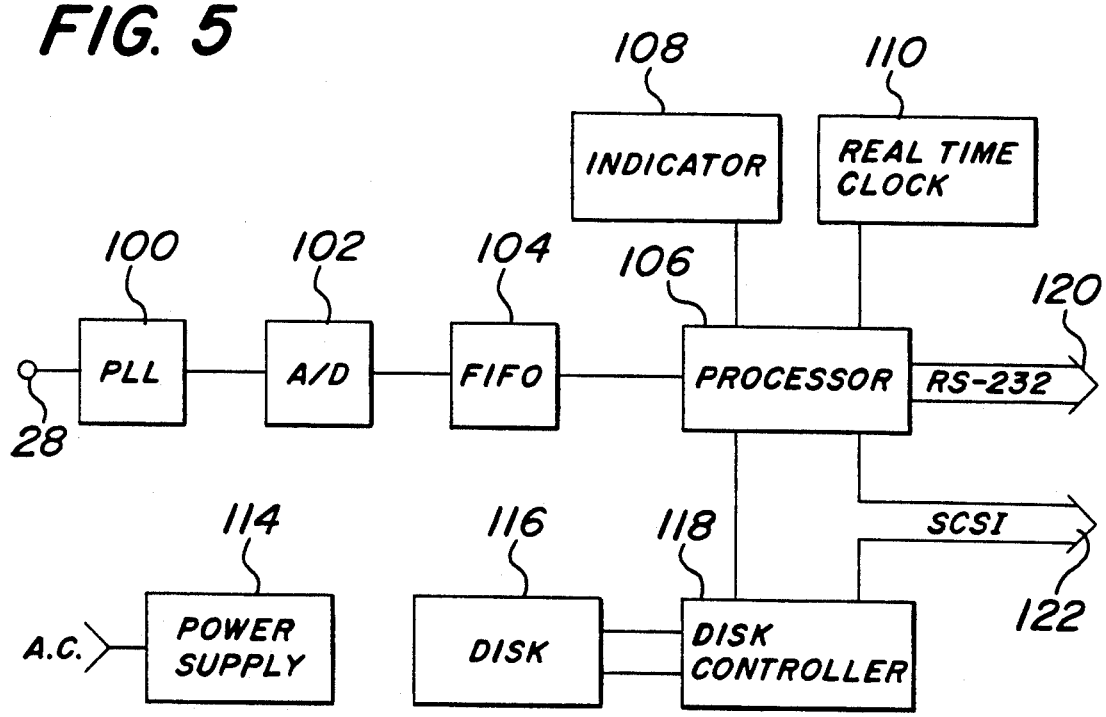
FIG. 5 is a block diagram of a portable auxiliary computer for use in the invention.

FIG. 5 is a block diagram of a portable auxiliary computer system which is desirably used with the previously described apparatus. This portable computer would generally be carried home by the patient, and used at certain times in conjunction with the recorder to perform several functions. First, the transportable auxiliary computer provides an increased data storage capability, such as on disk. This permits longer term monitoring, recording of more frequent events and/or recording more data in connection with each event. Second, the auxiliary computer includes signal processing software which, for practical reasons, has not been included in recorder 14. More specifically, the transportable auxiliary computer includes seizure and spike detection software. This permits data capture and storage upon the occurrence of predetermined types of EEG signals which may indicate a seizure or other event, regardless of whether the patient is able to actuate the push-button. For instance, the patient may interconnect the recorder 14 to the portable auxiliary computer 16 before going to sleep and the system will record waveform data for events occurring during the patient's sleep. Also, the patient can interconnect the recorder 14 to the auxiliary 16 while the patient is at home and awake but inactive. This permits recording of events which might be missed by the patient, and recording of event during which the patient is unable to actuate the push-button. Suitable seizure and spike detection software is commercially available.

It is expected that as larger static memories become available, all necessary memory might be included in recorder 14. At such time, it might be desirable also to transfer the seizure and spike detection software and other control and communication software from portable auxiliary computer 16 in the recorder 14.

In the portable auxiliary computer of FIG. 5, multiplexed EEG waveform data from recorder 14 is coupled via port 28 to phase locked loop 100. The phase locked output signal is coupled to A/D converter 102, where it is digitized, and the digitized output signal is coupled to FIFO buffer 104. Data output from FIFO buffer 104 is input to a processor 106, where it is analyzed in accordance with a seizure and spike detection algorithm to determine whether a seizure or spike event has taken place. Processor 106 is coupled via a SCSI bus to disk controller 118 for controlling storage of data on hard disk 116. In response to detection of an event, pre-event and post-event waveform data is stored on hard disk 116. A real time clock 110 for generation of time signals, and indicators 108, are coupled to processor 106. An RS-232 port 120 and a SCSI port 122 are also provided by processor 106, for communication with other devices such as a host computer as described later. Operating power for the portable computer is supplied by power supply 114, which may be powered from the AC mains since portable auxiliary computer 16 is not intended to be worn by the patient.

FIG. 6 is a software block diagram of the operating software of the recorder 14. A first portion of the software is stored in EEPROM, and a second portion of the software is a downloadable module which is stored in RAM prior to monitoring a patient. This module is downloaded from another auxiliary computer 16, which is referred to as a "host" computer. Such a host computer would generally be maintained at the place where monitoring electrodes are fitted to the patient. Such a host computer is provided to configure the portable auxiliary computer and the recorder for performing a particular monitoring procedure on a particular patient. The same or a similar host computer may be used to receive data after completion of monitoring, for analysis and generation of appropriate outputs.

The firmwire module stored in EEPROM 56 establishes communication with the host computer; controls timing of the multiplexer; configures the inputs and outputs; and loads and runs the downloadable module.

The downloadable module performs several functions in connection with operation of the system. It maintains a real time clock, derived from the microprocessor clock after initialization by the host computer. It maintains a delay buffer, used to temporarily store signals representing pre-event data. Such data will be stored as monitoring results if the push-button is actuated. It controls storage of waveform data, in response to a switch actuation or at periodic intervals. The downloadable module puts time of day data on the SYNC line, for communication to the portable auxiliary computer. It also monitors battery voltage, provides a watchdog timer, and performs error recovery in the event of a system error.

A patient parameter block is also downloaded. This block also includes data identifying the patient being monitored and the technician setting up the monitoring procedure; time of day; number of events saved; the electrode montage used; and the length of time before and after an event during which data will be stored.

In addition to storing waveform date occurring before and after a switch actuation, in a particularly preferred embodiment, the system also periodically stores waveform data for a short period of time. For instance, the system may store about 20 seconds of waveform data every 10 minutes. This enables later verification that the system likely was properly functional throughout the duration of the monitoring procedure.

Figure 7:
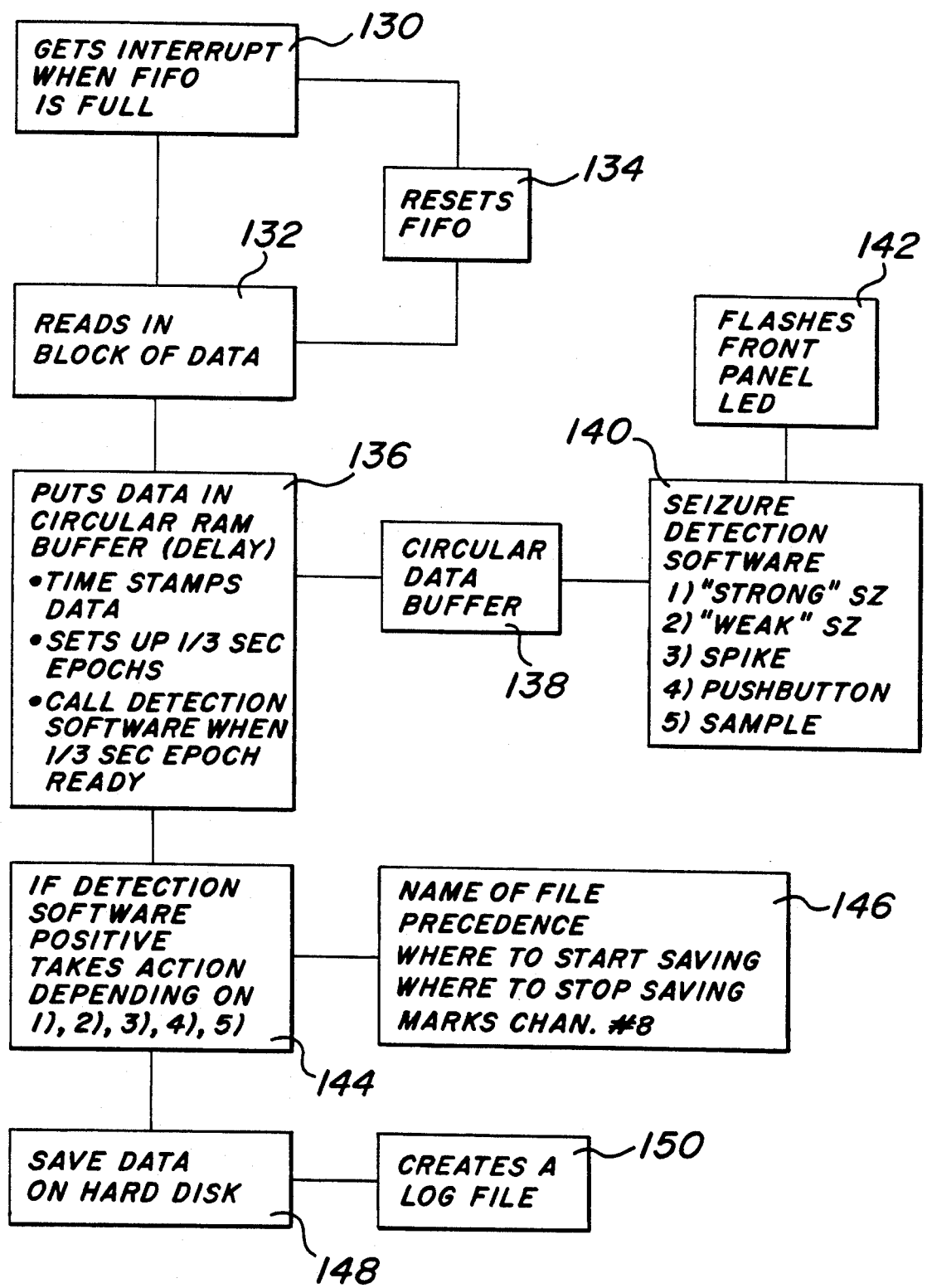
FIG. 7 is a software block diagram for a preferred auxiliary computer.

FIG. 7 shows a software block diagram illustrating the preferred operating software for the portable auxiliary computer. Blocks of waveform-related data are read into a FIFO buffer in blocks 130, 132, and 134. This data is placed in a circular RAM buffer, time stamped, and set up in epochs in blocks 136 and 138. The seizure and spike detection software of block 140 is then called and operates on the data in the buffer. This software determines whether a strong or weak seizure event or spike event has occurred, and whether the push-button has been actuated or the time for sampling has arrived. If such events have occurred, waveform data is stored on hard disk in steps 144, 146, and 148. The amount of data stored may be made variable in accordance with nature of the event which has occurred; for instance, less pre-event and post-event data may need to be stored in connection with a spike event than a seizure event. In step 146, a file name for the data to be stored is established in accordance with the type of event giving rise to the data. Rules of precedence are applied to determine how much data should be stored if events are overlapping. For instance, if a push-button event occurs during a sample interval, push-button actuation would be given precedence and data would be stored in accordance with the pre-event and post-event parameters established for push-button events, e.g. 2 minutes before and after push-button actuation. After determination of the amount of data to be saved, block 146 determines where the data that should be saved, and if data is being saved in response to push-button actuation, the time of actuation is marked on a particular channel (channel 8). Data is then saved to hard disk in step 148, and a log file entry is created in step 150 in connection with the event. Detection of a seizure or a spike event may also cause illumination of an indicator in step 142 to indicate this fact.

FIG. 8 is a flow diagram of preferred method for performing patient monitoring using the apparatus of the present invention. In step 160, a physician refers a patient for EEG services. In step 162, the patient is set up in a lab or the physician's office. In this step, electrodes and a transducer assembly are coupled to the patient, the transducer assembly is connected to the recorder, and the recorder, portable auxiliary computer, and host computer are interconnected. The downloadable module is loaded into the RAM in recorder 14 establishing operating and patient parameter information. Proper setup may be checked by applying a calibrating signal to the transducer, and the EEG waveforms may be viewed on a monitor coupled to the host computer for verification of proper setup. EEG waveform data may be stored and printed to provide reference or baseline data. Setup step 162 would also include any necessary communication with the patient regarding the monitoring procedure to be performed.

In step 164, the patient goes home with the patient-worn and transportable monitoring equipment previously described, and monitoring as described takes place for an extended period on the order of a day. In step 166, the patient returns to the lab or physician office and data store in the recorder or portable auxiliary computer is downloaded to a workstation auxiliary computer. The downloaded data is transmitted to an electroencephalographer in step 168, either as data or in the form of printout of EEG traces. The waveform data is reviewed by the electroencephalographer in step 170 and pertinent EEG waveform samples as well as a narrative report are sent to the referring physician.

Figure 9:
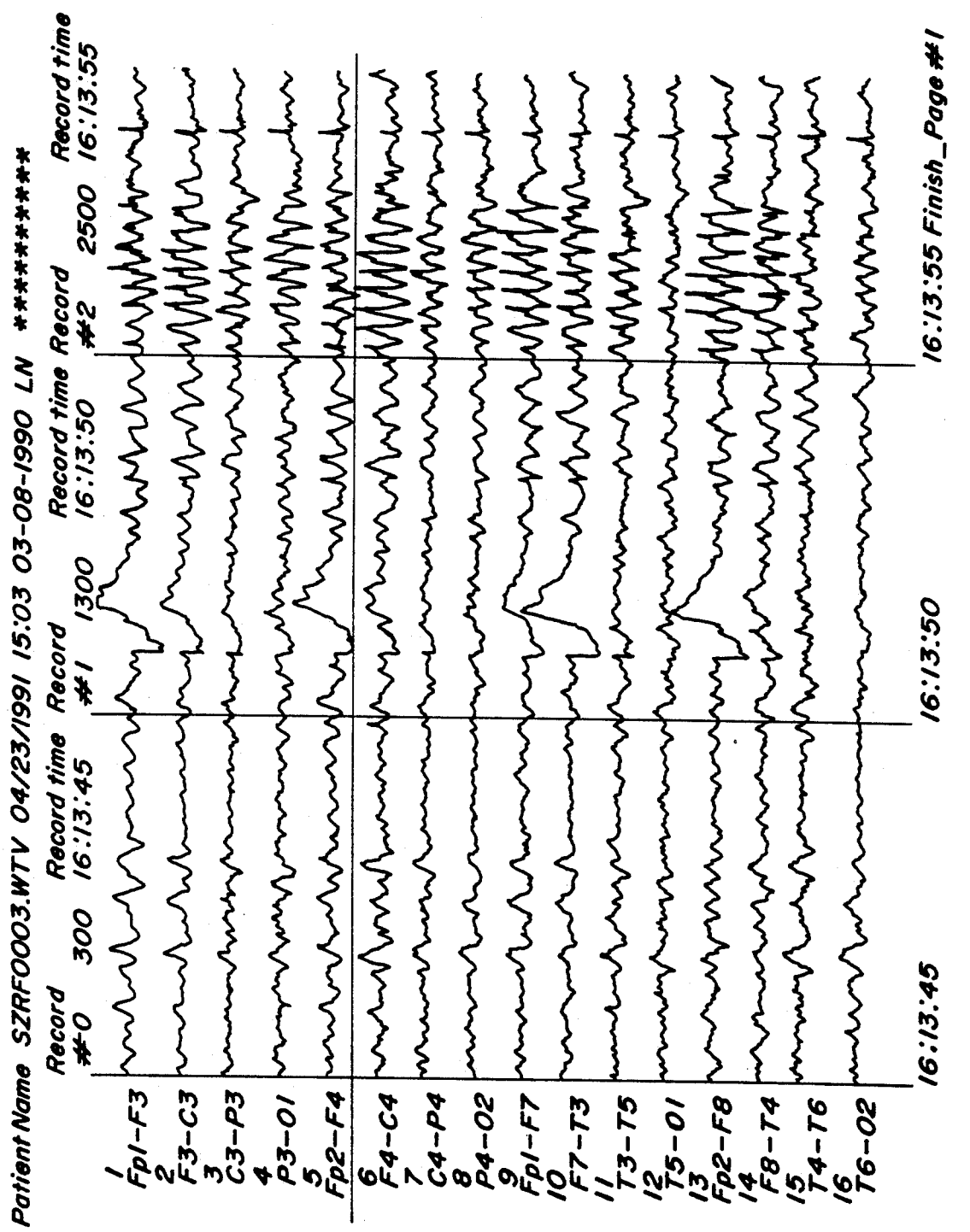
FIG. 9 is a representation of a printed output which may be generated by the invention.

By storage of waveform data in digital form, EEG information can be transmitted, processed, and printed by digital means, which provides for extremely high quality traces. In particular, graphic output may be provided by a laser printer. FIG. 9 shows a printout of the sort generated by the system of the present invention. In the preferred embodiment, the system prints information stored in the patient parameter block, such as montage and patient identifying information, as well as EEG traces.

FIG. 10 perspective illustration showing a preferred structure for the amplifier 34 and multiplexer 36 of the present invention. These components are housed within a housing 180 having a concave surface 182 having a curvature adapted to conform to the head of the patient being monitored. Thus, the curvature of surface 182 is desirably in the range of about 2 inches to about 5 inches. Connectors 184 are provided for connection of an electrode set 32 to the amplifiers. By placing the housing 180 on the top of the patient's head, the lengths of conductors connected to the electrodes may be minimized, which reduces the stray signal pick up of the system. After placement of the electrodes and the housing on the patient's head, they may be secured to the patient's head such as by wrapping it with a cloth. This minimizes stray signals caused by movement by electrodes or conductors during monitoring.

Further artifact reduction is desirably provided by an EMG filter, preferably a digital filter. Applicants have applied a known EMG filter algorithm to uploaded data in the host computer, but such a digital filter might also be included in the recorder or in the portable auxiliary computer. Less preferably, an analog EMG filter may be provided in one of these locations.

While particular embodiments of the invention have been shown and described, variations will no doubt occur to those skilled in the art without departing from the spirit or scope of the present invention.

What is claimed is:

1. A system for unattended ambulatory neurological monitoring of a patient comprising a neurological signal recording apparatus adapted to be worn by a patient during a monitoring procedure and operable when worn without electrical connection to any apparatus not worn by the patient, said recording apparatus including:

an input means for receiving a plurality of analog EEG signals, each derived from one pair of a plurality of pairs of electrodes coupled to a patient's head;

an A/D converter means having a converter input coupled to the apparatus input means and a converter output, said A/D converter means producing digital signals at said converter output which represent the waveforms of analog signals received at said converter input;

a digital memory means coupled to said converter output for storing digital data representing the waveforms of said analog EEG signals, said memory means storing all stored signals in digital form;

a controller means for controlling the storage of data in said memory means, said controller means causing temporary storage of data in said memory means representing the waveforms of EEG signals occurring over a predetermined interval of time representing a pre-event data storage interval and causing the periodic updating of the temporarily stored data to correspond with the data occurring in the predetermined interval immediately preceding each updating, said controller means further causing, upon the occurrence of a predetermined event, the permanent storage of data in said memory means including the temporarily stored data which represents the waveforms of EEG signals occurring over the pre-event data storage interval of time immediately preceding the event and data representing the waveforms of EEG signals occurring over an interval of time immediately following the event;

a self-contained power source means for providing operating power for said recording apparatus; and an output means coupled to said memory means for outputting digital waveform data derived from said stored data.

2. A system according to claim 1, wherein said recording apparatus includes a switch coupled to said controller means, and said predetermined event is actuation of said switch by said patient.

3. A system according to claim 1, wherein said recording apparatus includes a clock coupled to said controller means, and said controller means causes the storage of digital data representing the waveforms of EEG signals upon receipt by said controller means of a signal from said clock.

4. A system according to claim 1, wherein said recording apparatus includes signal processing apparatus coupled to said input and to said controller means, and said predetermined event is detection by said signal processing apparatus of predetermined electrical signals occurring at said input.

5. A system according to claim 4, wherein said signal processing apparatus includes means for detecting EEG signals corresponding to a waveform spike or a patient seizure.

6. A system according to claim 1, wherein said digital memory means is a semiconductor memory.

7. A system according to claim 6, wherein said digital memory means comprises static RAM.

8. A system according to claim 1, wherein said digital memory means comprises a magnetic disc.

9. A system according to claim 1, wherein said system includes artifact reduction means for reducing storage of data representing patient movement artifacts.

10. A system according to claim 9, wherein said artifact reduction means includes a digital memory which is unaffected by the patient's physical movement.

11. A system according to claim 9, wherein said artifact reduction means includes an electrical signal filter to remove EMG signal components.

12. A system according to claim 11, wherein said filter comprises an analog filter coupled to said input for filtering analog electrical signals.

13. A system according to claim 11, wherein said filter comprises a digital filter for receiving digital signals derived from said converter and producing filtered digital output signals.

14. A system according to claim 9, wherein said system includes a plurality of electrodes adapted to be coupled to a patient's body, and includes means for coupling neurological electrical signals generated by said patient to said recording apparatus input.

15. A system according to claim 14, wherein said artifact reduction means includes said coupling means.

16. A system according to claim 15, wherein said coupling means includes at least one amplifier having an input receiving said neurological signals and an output coupled to said recording apparatus input.

17. A system according to claim 16, wherein said amplifier is adapted to be mounted to the patient's head, whereby said amplifier input is close to electrodes to which it is coupled.

18. A system according to claim 17, wherein said coupling means includes a communication channel coupled to said recording apparatus input, and includes multiplexing means mounted to the patient's head and coupled to said amplifier for coupling neurological electrical signals from a plurality of said electrodes to said communication channel.

19. A system according to claim 15, wherein said amplifier is mounted in an enclosure having a curved surface having a radius of curvature in the range of about 2 inches to about 5 inches, whereby said enclosure may be placed adjacent the patient's head and generally conform to the surface thereof.

20. A system according to claim 14, wherein said artifact reduction means includes means for securing at least a portion of said coupling means to said patient's head.

21. A system according to claim 14, wherein said artifact reduction means includes adhesive means for securing said electrodes to said patient.

22. A system, according to claim 1, wherein said digital memory means includes means for separately storing data representing neurological electrical signals derived from at least 16 electrodes.

23. A system according to claim 1, wherein said digital memory means includes a storage capacity of at least about 1 Megabyte.

24. A system according to claim 23, wherein said digital memory means includes a storage capacity of at least about 4 Megabytes.

25. A system according to claim 1, wherein said recording apparatus includes means for simultaneously receiving and recording both EEG waveform signals and EKG signals.

26. A system according to claim 1, wherein said system includes a portable auxiliary computer system including auxiliary digital memory and not adapted to be worn by the patient, and also includes means for coupling said recording apparatus output to said auxiliary computer system for interchanging digital data between them.

27. A system according to claim 1, wherein said system includes a digital display generator means for receiving digital data stored in said recording apparatus and to generate a graphic digital display corresponding to received data.

28. A system according to claim 27, wherein said graphic digital display includes a graphic representation of EEG or EKG waveforms.

29. A system according to claim 27, wherein said digital display includes text representing information relating to said patient or to the neurological monitoring procedure performed on said patient.

30. A system according to claim 27, wherein said digital display generator means includes a laser printer.

31. A system according to claim 27, wherein said graphic display includes a representation of locations of said electrodes on said patient during the monitoring procedure.

32. A system according to claim 1, wherein said system includes means for storing data relating to said patient or to the neurological monitoring procedure performed on said patients.

33. A method of determining the neurological condition of a patient comprising the steps of:
a. when a patient is in a first location, securing a plurality of electrodes to the patient, said electrodes producing analog neurological electrical signals relating to said patient;
b. securing a recording apparatus including a digital memory to said patient;
c. coupling said electrodes to said recording apparatus;
d. when the patient is in a second location different from the first location, recording digital data in said memory including data responsive to said analog neurological electrical signals produced by said patient;
e. when the recording apparatus is in a third location, transferring digital data stored in recording step d to a computer system including a graphic display generator; and
f. generating a graphic digital display representing data transferred to said computer system in step e.

34. A method according to claim 33, wherein said first location and said third location are the same.

35. A method according to claim 33, wherein said securing step a includes securing at least about 16 electrodes to the patient's head.

36. A method according to claim 35, wherein said securing step a further includes securing at least one electrode to the patient's chest adjacent the patient's heart.

37. A method according to claim 33, wherein said securing step a includes gluing electrodes to said patient's skin.

38. A method according to claim 37, wherein said predetermined conditions include derived signals corresponding spike or seizure conditions of said patient.

39. A method according to claim 33, wherein said coupling step includes providing one or more conductors coupled to said electrodes and to said recording apparatus, and securing at least a portion of said conductors to said patient.

40. A method according to claim 33, wherein said securing step b includes securing to said patient a recording apparatus having a memory size of at least about 1 Megabyte.

41. A method according to claim 33, wherein said coupling step includes amplification of analog neurological electrical signals.

42. A method according to claim 41, wherein said coupling step includes disposing an amplifier contained in a curved housing, having a radius of curvature of between about 2 inches and about 5 inches, adjacent said patient's head.

43. A method according to claim 33, wherein said coupling step includes multiplexing of electrical signals derived from a plurality of said electrodes into a single communication channel.

44. A method according to claim 33, wherein said recording step includes an EMG signal filtration step.

45. A method according to claim 33, wherein said filtration step includes digital filtering.

46. A method according to claim 33, wherein said recording step includes recording digital data responsive to said analog electrical signals occurring over a period of at least about 12 hours.

47. A method according to claim 33, wherein said recording step includes recording data in response to a recording signal provided by said patient.

48. A method according to claim 33, wherein said recording step includes analyzing signals derived from said analog neurological electrical signals, and recording data in response to predetermined conditions of said derived signals.

49. A method according to claim 33, wherein said recording step includes intermittently recording data at predetermined times.

50. A method according to claim 33, wherein said display generating step includes generating a laser printed output.

51. A method according to claim 33, wherein said display generating step includes generating a graphic representation of EEG or EKG waveforms.

52. A method according to claim 33, wherein said display generating step includes generating text representing information relating to said patient or the neurological monitoring procedure performed on said patient.

53. A method according to claim 52, wherein said display generating step includes generating a graphic representation of the locations of said electrodes on said patient during said monitoring procedure.

* * * * *

UNITED STATES PATENT AND TRADEMARK OFFICE
CERTIFICATE OF CORRECTION

PATENT NO. : 5,222,503

DATED : June 29, 1993

INVENTOR(S) : John R. Ives and Norman R. Mainwaring

Figure 4D:
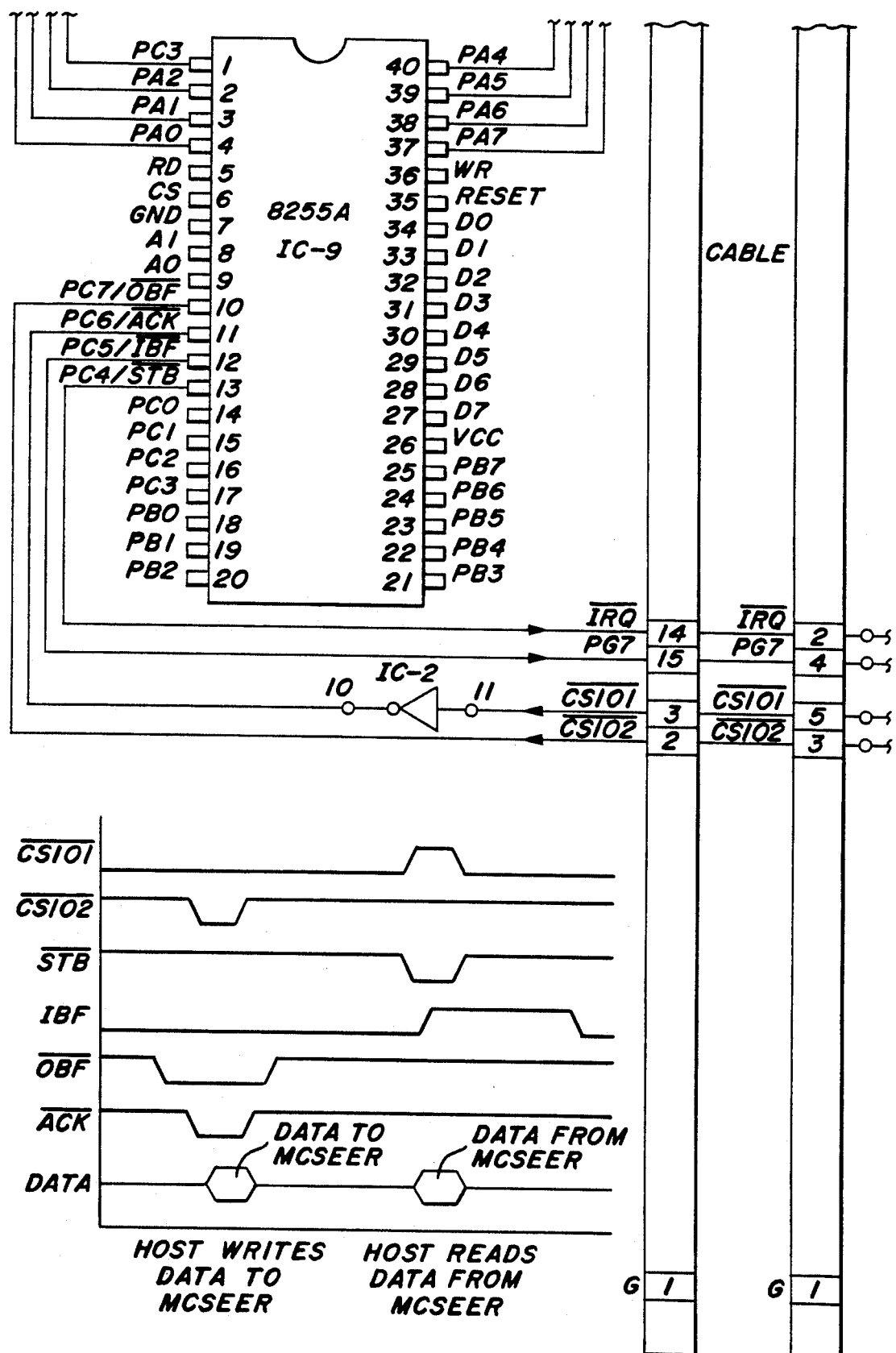
FIG. 4 is a schematic diagram of the preferred recording apparatus of the invention.
Figure 4E:
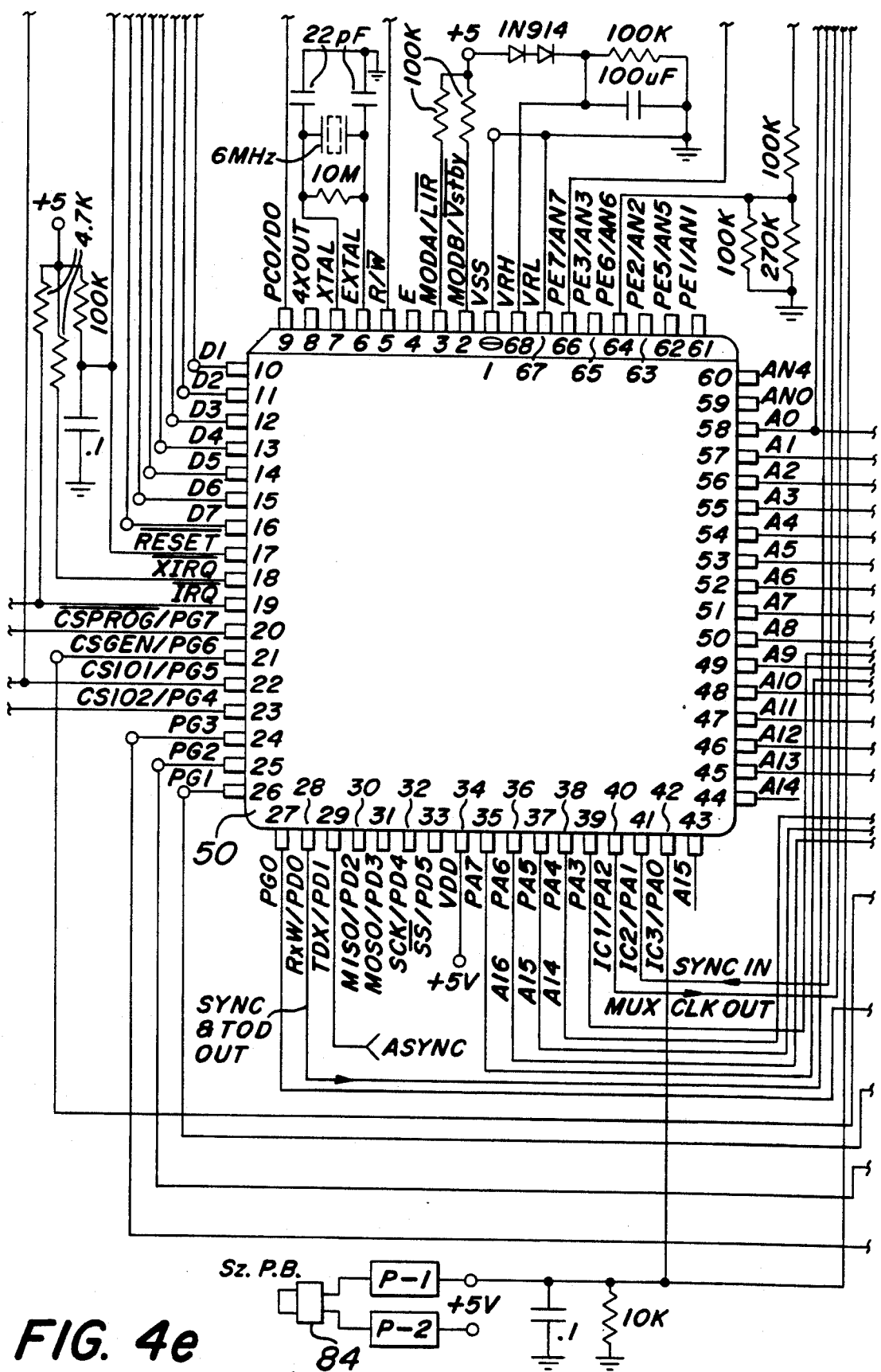
Figure 4F:
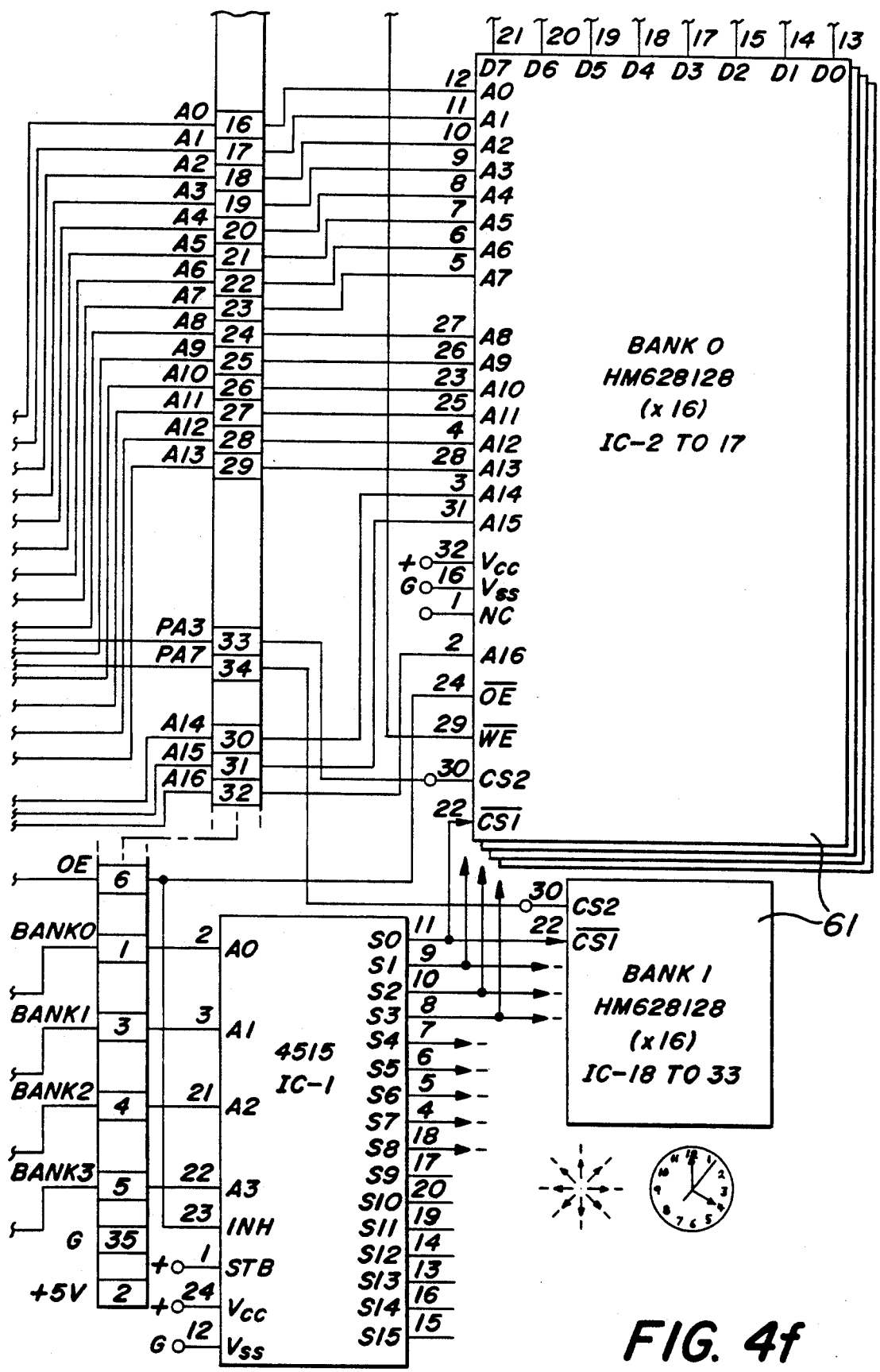

It is certified that error appears in the above-indentified patent and that said Letters Patent is hereby corrected as shown below:

Col. 6, line 54, delete "FIG. 4 shows" and substitute therefor --FIGS. 4a-4f show--.

Col. 7, line 6, delete "FIG. 4" and substitute therefor --FIGS. 4a-4f--.

Signed and Sealed this

Sixteenth Day of August, 1994

Attest:

BRUCE LEHMAN

Attesting Officer     Commissioner of Patents and Trademarks